US012599590B2

(12) United States Patent
Brennan et al.

(10) Patent No.: US 12,599,590 B2
(45) Date of Patent: Apr. 14, 2026

(54) VETERINARY FORMULATIONS COMPRISING RAPAMYCIN AND METHODS OF USING THE SAME FOR TREATING ANIMAL DISEASE

(71) Applicant: TriviumVet DAC, Waterford (IE)

(72) Inventors: Tom Brennan, Clonmel (IE); Louise Grubb, Tramore (IE); Liam Byrne, Waterford (IE); Stuart Fitzgerald, Waterford (IE)

(73) Assignee: TriviumVet DAC, Waterford (IE)

( * ) Notice: Subject to any disclaimer, the term of this patent is extended or adjusted under 35 U.S.C. 154(b) by 664 days.

(21) Appl. No.: 17/777,800

(22) PCT Filed: Dec. 18, 2020

(86) PCT No.: PCT/IB2020/062204
§ 371 (c)(1),
(2) Date: May 18, 2022

(87) PCT Pub. No.: WO2021/124264
PCT Pub. Date: Jun. 24, 2021

(65) Prior Publication Data
US 2022/0401421 A1     Dec. 22, 2022

Related U.S. Application Data

(60) Provisional application No. 62/950,480, filed on Dec. 19, 2019.

(51) Int. Cl.
| | |
|---|---|
| *A61K 31/436* | (2006.01) |
| *A61K 9/20* | (2006.01) |
| *A61K 9/28* | (2006.01) |
| *A61K 31/675* | (2006.01) |

(52) U.S. Cl.
CPC .......... *A61K 31/436* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 9/2077* (2013.01); *A61K 9/2813* (2013.01); *A61K 9/282* (2013.01); *A61K 9/2846* (2013.01); *A61K 31/675* (2013.01)

(58) Field of Classification Search
CPC .. A61K 31/436; A61K 9/2013; A61K 9/2018; A61K 9/2027; A61K 9/2031; A61K 9/2054; A61K 9/2077; A61K 9/2813; A61K 9/282; A61K 9/2846; A61K 31/675; A61P 9/00
See application file for complete search history.

(56) References Cited

U.S. PATENT DOCUMENTS

| | | | | |
|---|---|---|---|---|
| 5,496,832 | A * | 3/1996 | Armstrong | A61K 31/436 |
| | | | | 514/291 |
| 6,197,781 | B1 | 3/2001 | Guitard et al. | |
| 2008/0199896 | A1 | 8/2008 | Guan | |
| 2008/0275076 | A1* | 11/2008 | Holm | A61K 9/1652 |
| | | | | 514/291 |
| 2009/0130210 | A1* | 5/2009 | Raheja | A61K 31/4355 |
| | | | | 424/494 |
| 2010/0098770 | A1* | 4/2010 | Ramalingam | A61K 31/4355 |
| | | | | 514/2.4 |
| 2010/0152531 | A1* | 6/2010 | Goodman | A61F 2/2481 |
| | | | | 600/37 |
| 2013/0095144 | A1* | 4/2013 | Roy | A61K 9/1623 |
| | | | | 514/291 |
| 2017/0348270 | A1* | 12/2017 | Vaughn | A61P 25/28 |
| 2018/0353488 | A1* | 12/2018 | Seward | A61P 9/04 |

FOREIGN PATENT DOCUMENTS

| | | | |
|---|---|---|---|
| WO | WO-2006/039237 A1 | 4/2006 | |
| WO | WO-2006/094507 A1 | 9/2006 | |

OTHER PUBLICATIONS

Shioi, T., et al.; "Rapamycin Attenuates Load-Induced Cardiac Hypertrophy in Mice", Circulation, American Heart Association, Inc., US, vol. 107, No. 12, Apr. 1, 2003, pp. 1664-1670.
Urfer, S. R., et al.; "A randomized controlled trial to establish effects of short-term rapamycin treatment in 24 middle-aged companion dogs", Geroscience, Springer International Publishing, Cham, vol. 39, No. 2, Apr. 3, 2017, pp. 117-127.
International Search Report from corresponding PCT Application No. PCT/IB2020/062204, dated Feb. 24, 2021.
Office Action from corresponding European Patent Application No. 20 828 864.7, dated Apr. 15, 2024.
Maderuelo, C., et al.; "Enteric coating of oral solid dosage forms as a tool to improve drug bioavailability", European Journal of Pharmaceutical Sciences 138 (2019) 105019, pp. 1-15.
International Preliminary Report on Patentability (IPRP) & Written Opinion of the International Searching Authority from corresponding PCT Application No. PCT/IB2020/062204, dated Jul. 30, 2022.

* cited by examiner

*Primary Examiner* — Frederick F Krass
*Assistant Examiner* — Abdulrahman Abbas
(74) *Attorney, Agent, or Firm* — Hovey Williams LLP

(57) ABSTRACT

The present disclosure provides veterinary formulations comprising rapamycin or rapalogs for administration to companion animals and methods of using the formulations to treat cardiac dysfunction, including hypertrophic cardiomyopathy, dilated cardiomyopathy, mitral valve disease, pressure-overload cardiac hypertrophy, cancer, effects of aging, inflammatory disease, and viral infection.

15 Claims, 16 Drawing Sheets

- Fractional Shortening (FS) – measure of systolic function
- Ejection Fraction (EF)
- E/A ratio – measure of diastolic function

VETERINARY FORMULATIONS COMPRISING RAPAMYCIN AND METHODS OF USING THE SAME FOR TREATING ANIMAL DISEASE

CROSS-REFERENCE TO RELATED APPLICATIONS

This application is a national phase entry of PCT Application No. PCT/IB2020/062204, filed on 18 Dec. 2020, which claims the benefit of and priority to U.S. patent application Ser. No. 62/950,480, filed on Dec. 19, 2019. The entire disclosure of the applications identified in this paragraph are incorporated herein by references.

FIELD

The present disclosure relates to veterinary compositions comprising rapamycin and methods of using the same for improving health, such as cardiac health, and reducing the effects of aging in animals.

BACKGROUND

This section provides background information related to the present disclosure which is not necessarily prior art.

The mechanistic (or mammalian) target of rapamycin (mTOR) pathway plays a key regulatory function in cardiovascular physiology and pathology. Pharmacologic and genetic inhibition of the mTOR complex 1 (mTOC1) has been shown to reduce pathological hypertrophy and heart failure, reduce myocardial damage after myocardial infarction, and reduce cardiac derangements caused by metabolic disorders. Inhibiting mTOC1 increases autophagy and extends lifespan. Partial and selective inhibition of mTORC1 has been shown to be cardioprotective during aging and is associated with a number of beneficial and protective effects in the published literature including: improving markers of cardiac health/function, reducing cardiac hypertrophy under pressure overload and in presence of cardiomyopathies, reducing ischemic injury after myocardial infarction, and stimulating cardiac autophagy. Pharmacologic inhibition of mTOC1 decreases heart dimensional measures, such as left ventricular internal diameter (LVIDd) and overall heart mass.

Rapamycin (also known as sirolimus or Rapamune®) is an inhibitor of mTOR and mTOC1. Rapamycin is poorly soluble in water. Although it is permeable in the intestines, it undergoes a high degree of efflux. Moreover, it is acid-labile and rapidly degrades within the typical gastric pH range. Oral formulations of rapamycin show highly variable pharmacokinetic properties and poor absolute bioavailability.

Long-term rapamycin treatment in mice extends lifespan and effectively reverses pre-existing cardiac hypertrophy and diastolic function. Companion animals, such as dogs and cats, experience age-related cardiovascular deterioration, including reduced stroke volume and cardiac output and an increased risk of degenerative valve disease. Urfer, et al. (*Geroscience,* 2017; 39(2):117-127) reports that rapamycin may partially reverse age-related heart dysfunction in healthy dogs. Long-term treatment with low, non-immuno-suppressive doses of rapamycin (up to 1.0 mg/kg/day) are well tolerated in dogs.

Hypertrophic cardiomyopathy (HCM) is one of the most commonly encountered heart disease in cats. This disease is characterized by an abnormal thickening (hypertrophy) of one or several areas of the walls of the heart, usually of the left ventricle.

U.S. Pat. No. 5,496,832 reports a method for treating myocarditis, cardiomyopathy, endocarditis, or pericarditis in a mammal comprising administration of rapamycin. However, companion animals are not directly disclosed.

SUMMARY

This section provides a general summary of the disclosure, and is not a comprehensive disclosure of its full scope or all of its features.

The present disclosure provides veterinary formulations of rapamycin, and methods of using the formulation to treat companion animals for cardiac disease, cancer, effects of aging, inflammatory disease, and viral infection.

In an embodiment, there is provided a method for treating hypertrophic cardiomyopathy, dilated cardiomyopathy, mitral valve disease, or pressure-overload cardiac hypertrophy in companion animals, the method comprising: administering to the companion animal in need thereof a composition comprising a therapeutically effective amount of rapamycin or pharmaceutically acceptable salts thereof. In an embodiment, the composition comprises a therapeutically effective amount of rapamycin in a dispersion, which is then combined with a binder, and a polymer, an extra-granular part comprising a polymer, and a coating. In some embodiments, the method uses about 0.4 mg to about 3 mg rapamycin.

In an embodiment, the companion animal is a dog or a cat.

In another embodiment, there is provided a veterinary composition comprising: about 0.4 mg to about 3 mg rapamycin, and poloxamer, alpha-D-tocopherol, povidone, and a flavoring agent.

BRIEF DESCRIPTION OF THE DRAWINGS

The drawings described herein are for illustrative purposes only of selected embodiments and not all possible implementations, and are not intended to limit the scope of the present disclosure.

DETAILED DESCRIPTION

Figure 1:
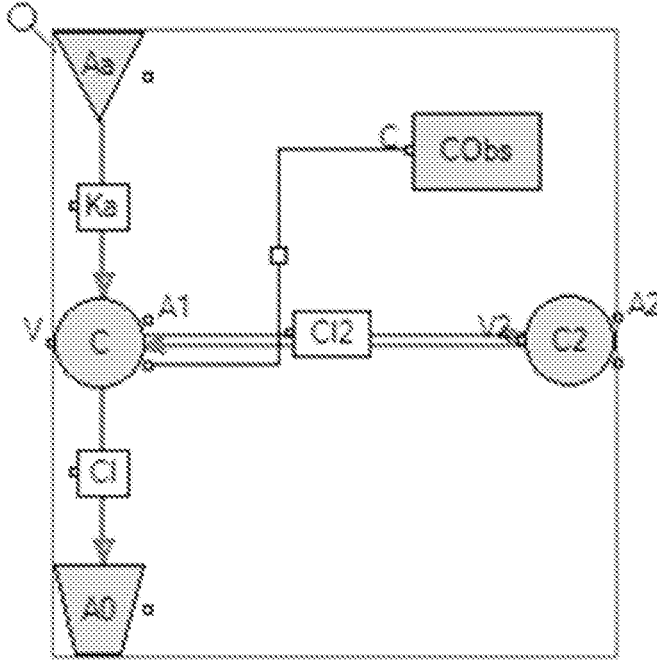
FIG. 1 describes a pharmacokinetic model of rapamycin in dogs.

The following description is merely exemplary in nature and is not intended to limit the present disclosure, application, or uses.

The term "rapamycin" refers to the macrolide antibiotic that is also known as "sirolimus" or "Rapamune®)." Unless otherwise described, rapamycin includes the compound and veterinary or pharmaceutically acceptable salts thereof, as well as analogs of rapamycin (conventionally known as "rapalogs"), including, but not limited to temsirolimus, everolimus, and ridaforolimus.

The term "cardiac dysfunction" means any diseases, disorders, or conditions of the heart, including age-related diseases, disorders, or conditions related to the heart. In some embodiments, cardiac dysfunction includes cardiomyopathy, such as hypertrophic cardiomyopathy (HCM) or dilated cardiomyopathy (DCM); valve disease, such as mitral valve disease (MVD); and cardiac hypertrophy, such as pressure-overload hypertrophy.

Dilated cardiomyopathy is a disease of the myocardium that results in the mechanical dysfunction and/or electrical dysfunction. DCM may be defined by: (i) left ventricular dilatation; (ii) reduced systolic function; and (iii) increased sphericity of the left ventricle. Development of DCM is slow and few clinical signs manifest over time. As DCM progresses, signs include lethargy, anorexia, shallow breathing, sudden fainting, and potential death. The clinical stage of DCM may be subtle and is typically characterized by signs of congestive heart failure, with or without cardiac arrhythmias. DCM occurs most commonly in medium and large breed dogs, and causes progressive congestive heart failure. The functional classification for heart failure is summarized by the New York Heart Association (NYHA) classification, summarized in Table 1:

TABLE 1

| | |
|---|---|
| Class I | Patients with asymptomatic heart disease (e.g., CVHD is present but no clinical signs are evident, even with exercise). |
| Class II | Patients with heart disease that causes clinical signs only during strenuous exercise. |
| Class III | Patients with heart disease that causes clinical signs with routine daily activities or mild exercise. |
| Class IV | Patients with heart disease that causes sever clinical signs, even at rest. |

The American College of Veterinary Internal Medicine (ACVIM) developed a newer classification system to more objectively categorize animals in the course of their heart disease, linking the severity of the signs to appropriate treatments at each stage. According to the ACVIM, the stages include:

Stage A: Animals at high risk for heart disease (no disease present).

Stage B: A murmur is heard but there are no visible signs of heart failure.

Stage B1: The heart does not appear enlarged or changed on X-ray.

Stage B2: The heard appears enlarged or changed on X-ray.

Stage C: Evidence of heart failure is visible and treatment is necessary.

Stage D: Heart failure is getting hard to manage and is not responding to standard treatment.

Mitral valve disease can take years to develop for first diagnosis, and can sometimes present with congestive heart failure. Clinical signs of MVD are similar to DCM and include left apical systolic heart murmur, left-sided congestive heart failure (including tachypnea, cough, exercise intolerance, syncope, and respiratory distress), arrhythmias, and poor appetite.

The term "effects of aging" include diseases, disorders, and conditions associated with aging in companion animals, such as in cats and dogs. The effects of aging include cognitive decline, cognitive dysfunction, dementia, cancer, respiratory illness, autoimmune diseases, immunosenescence, energy storage diseases, benign prostatic hyperplasia, a reduction in vitality, and age-associated behavioral disorders. The term "cancer" encompasses tumors and cancers common in companion animals and includes, mast cell tumors, melanoma, lymphoma, osteosarcoma, hemangiosarcoma, squamous cell carcinoma, benign prostatic hyperplasia, and soft-tissue sarcoma.

The term "inflammatory diseases" include diseases, disorders, and conditions that are due to an overactive or improper inflammation. Inflammatory diseases include, but are not limited to, dermatitis, chronic bronchitis, hepatitis, chronic inflammation, and inflammatory bowel disease.

The term "treat" (and corresponding terms "treatment" and "treating") includes palliative, restorative, and preventative treatment of a subject. The term "palliative treatment" refers to treatment that eases or reduces the effect or intensity of a condition in a subject without curing the condition. The term "preventative treatment" (and the corresponding term "prophylactic treatment") refers to treatment that prevents the occurrence of a condition in a subject. The term "restorative treatment" refers to treatment that halts the progression of, reduces the pathologic manifestations of, or entirely eliminates a condition in a subject.

The terms "prevent", "prevention", or "preventing" refer to either preventing the onset of preclinically evident condition altogether or preventing the onset of a preclinical evident stage of a condition in a subject. Prevention includes, but is not limited to, prophylactic treatment of a subject at risk of developing a condition.

The term "therapeutically effective amount" refers to an amount of a compound that, when administered to a subject for treating or preventing a disease, is sufficient to effect treatment for or prevention of the disease. "Therapeutically effective amount" can vary depending on the compound, the disease and its severity, the species, the age, the weight, etc. of the subject to be treated. In particular embodiments, the therapeutically effective amount of rapamycin treats dilated cardiomyopathy, hypertrophic cardiomyopathy, mitral valve disease, and/or pressure-overload cardiac hypertrophy in companion animals, such as dogs and cats.

The term "companion animals" refers to domesticated animals living in the same quarters as humans. Companion animals, commonly referred to as pets, includes dogs, cats, horses, birds, rabbits, goats, and gerbils. In particular embodiments, the companion animal is a dog or a cat, including all breeds thereof.

The term "veterinary composition" refers to compositions suitable for administration to animals, such as companion animals. Veterinary compositions include an active agent and veterinary acceptable excipients. In some embodiments, the active agent is rapamycin, or salts thereof. In some embodiments, the acceptable excipients include poloxamer, sucrose, microcrystalline cellulose, alpha-tocopherol (including alpha-D-tocopherol, alpha-L-tocopherol, and alpha-D,L-tocopherol, and acetate salts thereof), lactose, crospovidone, povidone, citric acid, talc, flavor, and combinations of two or more thereof. In some embodiments, the flavor is beef flavor, chicken flavor, lamb flavor, or fish flavor. The flavor may be natural or artificial.

Compositions

The compositions of the present disclosure include veterinary compositions comprising rapamycin, rapalogs, or salts thereof, and appropriate excipients. The rapamycin is present in the compositions at a therapeutically effective amount. In an embodiment, the composition comprises between about 0.4 and about 3 mg rapamycin. In particular embodiments, the composition comprises about 0.4 mg, about 0.5 mg, about 1.0 mg, about 1.2 mg, about 1.5 mg, about 2.0 mg, about 2.4 mg, about 2.5 mg, or about 3.0 mg rapamycin. The total tablet weight may be between about 50 and about 360 mg. In particular embodiments, the total tablet weight is about 60-70 mg, about 80-90 mg, about 90-100 mg, about 160-180 mg, or about 330-360 mg.

In some embodiments, the rapamycin is present in a dispersion that is mixed with other excipients, granulated, and incorporated into a tablet. In further embodiments, the rapamycin dispersion has a size of $D_{90}$ of about 2 µm to about 30 µm. In a particular embodiment, the $D_{90}$ is about 2 µm to about 5 µm.

In some embodiments, the composition comprises poloxamer, alpha-D-tocopherol, in a dosage form with gastro-resistant coating. Further embodiments may additionally comprise one or more of sucrose, microcrystalline cellulose, lactose, crospovidone (which may include one or more grades of crospovidone), and povidone (which may include one or more grades of povidone). In particular embodiments, the composition comprises a flavor or flavoring agent, such as a beef, chicken, lamb, or fish flavor.

In some embodiments, the veterinary composition is selected from immediate release, sustained release, pulsed release, delayed release, and combinations thereof. In a particular embodiment, the veterinary composition is a delayed release formulation. The release profile of the veterinary composition may be determined by the coating. In some embodiments, the coating comprises one or more ingredients selected from the group consisting of a polymer or copolymer (including methacrylic acid ethyl acrylate copolymer), talc, titanium dioxide, triethyl citrate, silica (including colloidal anhydrous silica), a base (including sodium bicarbonate), a detergent (including sodium lauryl sulfate), a dye, and combinations thereof.

In a particular embodiment, the composition comprises a rapamycin dispersion, an extra-granular part, and a functional delayed-release coating. In some embodiments, the rapamycin dispersion comprises rapamycin, a polymer, and a binder. The dispersion may further comprise a sugar. The polymer of the dispersion may be a cellulosic polymer, such microcrystalline cellulose, HPMC, or a non-cellulosic polymer, such as a polyvinylpyrrolidone (i.e. povidone, polyplasdone XL, polyplasdone XL10). The sugar includes one or more selected from the group consisting of sucrose, lactose, mannitol, glycosaminoglycan. The binder may comprise a single component or multiple components. Binders may be selected from one or more of glycerides, poloxamers, tocopherols, polymers, and organic acids (including anhydrous organic acids). In some embodiments, the binder is selected from the group consisting of poloxamer, glycerol monooleate, alpha-DL-tocopheryl acetate, povidone K-30, and citric acid (which may be anhydrous or a hydrate thereof). In some embodiments, the extra-granular part comprises one or more polymers, including a cellulosic polymer (such as microcrystalline cellulose) or a non-cellulosic polymer (such as polyplasdone XL10 or polyplasdone XL), or other excipients (such as talc, silica, magnesium stearate).

In some embodiments, the rapamycin dispersion represents about 45 wt % to about 90 wt % of the total weight of the preparation, about 50 wt % to about 80 wt % of the total weight of the preparation, about 55 wt % of the total weight of the preparation, about 75 wt % of the total weight of the preparation, or about 72 wt % of the total weight of the preparation.

In some embodiments, the polymer represents about 40 wt % to about 75 wt % of the total weight of the preparation, or about 55 wt % of the total weight of the preparation. In some embodiments, the sugar represents about 20 to about 40 wt % of the total weight of the preparation, about 35 wt % of the total weight of the preparation or about 36 wt % of the total weight of the preparation. In some embodiments, the binder represents about 1 wt % to about 10 wt % of the total weight of the preparation, about 4.6 wt %, about 5.2 wt % or about 5.5 wt % of the total weight of the preparation. In some embodiments, the rapamycin and binder represent about 5 wt % to about 15 wt % of the total weight of the preparation, about 7 wt % to about 12 wt % of the total weight of the preparation, about 7.5 wt % to about 9.5 wt % of the total weight of the preparation, about 7.5 wt % of the total weight of the preparation, or about 9.5 wt % of the total weight of the preparation.

In some embodiments, the extra-granular part represents about 10 wt % to about 20 wt % of the total weight of the preparation or about 15 wt % of the total weight of the preparation.

In a particular embodiment, the formulation comprises microcrystalline cellulose, polyplasdone XL, and sucrose; rapamycin; a binder comprising poloxamer, glyceryl monooleate, alpha-DL-tocopheryl acetate, povidone K-30, and citric acid anhydrous; an extra-granular part comprising microcrystalline cellulose, polyplasdone XL, polyplasdone XL10, and talc; and the coating comprises methacrylic acid ethyl acrylate copolymer, talc, titanium dioxide, triethyl citrate, colloidal anhydrous silica, sodium bicarbonate, and a detergent.

In another embodiment, the composition comprises rapamycin, lactose, microcrystalline cellulose, sodium starch glycolate, a flavoring agent, and magnesium stearate. In another embodiment, the composition comprises rapamycin, silica, lactose, microcrystalline cellulose, sodium starch glycolate, a flavoring agent, and magnesium stearate. In another embodiment, the composition comprises rapamycin, silica, lactose, microcrystalline cellulose, sodium starch glycolate, a flavoring agent, and magnesium stearate. In a particular embodiment, the composition comprises rapamycin, gelatin, mannitol, and a flavoring agent.

In some embodiments, the rapamycin composition is formulated specifically for dogs or cats. In a particular embodiment, the dog or cat specific formulation comprises rapamycin, microcrystalline cellulose, sucrose, povidone, crospovidone, poloxamer 188, glycerol monooleate, alpha-D-tocopherol, talc, and an artificial flavor.

The compositions of the present disclosure can be administered via any appropriate route, including oral, buccal, nasal, topical, and rectal. In a particular embodiment, the composition is formulated for oral administration, such as in the form of a tablet. Furthermore, the composition can formulated for immediate release, sustained release, delayed release, pulsatile release, controlled release, and combinations thereof.

The compositions of the present disclosure can be formulated in various formulations. In one embodiment, the composition is a solid dispersion. In another embodiment, the composition is loaded onto silica carrier material (via either solvent evaporation or a dry loading process). In yet another embodiment, the composition is formulated as lyotablets prepared via a freeze-drying process.

Treatment

The compositions of the present disclosure are administered for the treatment of cardiac dysfunction in companion animals. In some embodiments, the cardiac dysfunction includes hypertrophic cardiomyopathy, dilated cardiomyopathy, mitral valve disease, and pressure-overload cardiac hypertrophy.

In some embodiments, compositions of the present disclosure are administered for the treatment of at least one of cancer, effects of aging, inflammatory disease, diabetes, and viral infection in a companion animal.

In one embodiment, the subject is a dog suffering from DCM.

In one embodiment, the subject is a dog suffering from MVD.

In one embodiment, the subject is a dog suffering from HCM

In one embodiment, the subject is a dog suffering from pressure-overload cardiac hypertrophy.

In one embodiment, the subject is a cat suffering from HCM.

In one embodiment, the subject is a cat suffering from a viral infection, including feline immunodeficiency virus infection.

The compositions of the present disclosure may also be administered to ameliorate the effects of aging. In particular embodiments, the effects of aging include cognitive decline, cognitive dysfunction, dementia, cancer, respiratory illness, autoimmune diseases, energy storage diseases, a reduction in vitality, and age-associated behavioral disorders.

In some embodiments, the companion animal is treated with rapamycin in an amount ranging from about 0.025 mg/kg to about 0.75 mg/kg. In some embodiments, the companion animal is treated with an amount ran amount 0.05 mg/kg to about 0.25 mg/kg. In some embodiments, the companion animal is treated in an amount ranging from 0.1 mg/kg to about 0.2 mg/kg.

In some embodiments, the companion animal is treated daily, every other day, three times a week, and/or weekly.

EXAMPLES

Example 1: Companion Animal-Specific Formulations

Exemplary embodiments of delayed release companion-animal specific formulations are shown in Table 2 below.

TABLE 2

| Name of Ingredients | 2.4 mg mg/tab | 1.2 mg mg/tab | 0.4 mg mg/tab |
|---|---|---|---|
| Intra Granular Part | | | |
| Microcrystalline cellulose | 34.45 | 36.25 | 23.75 |
| Crospovidone | 2.00 | 2.00 | 1.25 |
| Sucrose | 32.00 | 32.00 | 22.00 |
| Total Weight | 68.45 | 70.25 | 47.00 |
| API Dispersion | | | |
| Rapamycin (API) | 2.40 | 1.20 | 0.40 |
| Poloxamer | 1.20 | 0.60 | 0.20 |
| Purified water * | q.s. | q.s. | q.s. |
| Binder Preparation | | | |
| Poloxamer | 0.05 | 0.05 | 0.05 |
| Glyceryl Mono-oleate | 0.10 | 0.10 | 0.10 |
| Tocopheryl Acetate | 1.00 | 1.00 | 1.00 |
| Povidone | 1.40 | 1.40 | 1.00 |
| Citric acid | 1.00 | 1.00 | 1.00 |
| Purified water * | q.s. | q.s. | q.s. |
| Total Weight | 75.60 | 75.60 | 50.75 |
| Extra-Granular | | | |
| Microcrystalline cellulose | 4.00 | 4.00 | 2.50 |
| Crospovidone | 9.0 | 9.0 | 5.75 |
| Talc | 1.40 | 1.40 | 1.00 |
| Total Weight (Core Tablets) | 90.00 | 90.00 | 60.00 |
| Coating | | | |
| Coating | 7.00 | 7.00 | 7.00 |
| Total Weight (Enteric coated Tablets) | 97.00 | 97.00 | 64.50 |

* water evaporates on drying and, if present in final product, is only present in trace amounts.

In the compositions of Table 1, the coating comprises methacrylic acid ethyl acrylate copolymer, talc, titanium dioxide, triethyl citrate, colloidal anhydrous silica, sodium bicarbonate, sodium lauryl sulfate and, one or more colorants.

The 2.4 mg rapamycin tablet was prepared as follows:

Preparation of rapamycin dispersion: Poloxamer was dissolved in purified water under mechanical stirring until homogenous. Rapamycin was added to the poloxamer solution and homogenized in a high shear homogenizer and then further homogenized under several alternating high-pressure cycles Binder preparation: Tocopheryl acetate, glyceryl mono-oleate, and poloxamer were mixed with purified water and homogenized. The tocopheryl acetate/glyceryl mono-oleate/poloxamer solution was added to the rapamycin dispersion and the mixture was stirred until uniformly mixed. Citric acid and povidone were separately dissolved in water, and then added to the rapamycin solution. This mixture was dried to achieve a level of dryness (LOD) of less than 3.5%.

Extra-granular material preparation: microcrystalline cellulose, sucrose, and crospovidone were sieved through a suitable size sieve and mixed until uniform.

The extra-granular material was added to the dried, rapamycin-containing mixture and mixed until uniform. Talc was sifted through a suitable size sieve and added to the blend.

The total mixture was compressed into tablets using 6 mm round, standard concave tooling plane with an average weight of 90 mg±5%. The tablets were coated by an autocoater. The coating solution was prepared by mixing methacrylic acid ethyl acrylate copolymer, talc, titanium dioxide, triethyl citrate, colloidal anhydrous silica, sodium bicarbonate, sodium lauryl sulfate and, one or more colorants and adding the mixture to purified water and mixing for about 45 minutes to achieve a uniform dispersion. The average weight of the coated tablets was 97 mg±5%.

The 1.2 mg and 0.4 mg tablets were prepared as above, with adjustments to the amount of microcrystalline cellulose to compensate for the reduced amount of rapamycin. The 0.4 mg tablet has a final average weight of 64.5±5%.

Example 2A: Additional Companion Animal Specific Formulations

An example of a companion animal specific formulation is show in Table 3 below.

TABLE 3

| Ingredient | Amount (w/w) |
| --- | --- |
| Rapamycin | 0.4-0.8% |
| Microcrystalline Cellulose | 40-60% |
| Sucrose | 30-50% |
| Povidone | 0.5-5% |
| Crospovidone | 5-15% |
| Poloxamer 188 | 0.5-2.0% |
| Glycerol Monooleate | 0.01-0.1% |
| Alpha-D-Tocopherol | 0.01-0.15% |
| Talc | 0.5-2.0% |
| Artificial Flavor | 0.5-2.5% |

Example 2B: Solid Dispersion (Via Solvent Evaporation Process)

Dissolve Rapamycin in (organic) solvents and cast on filler and/or binder excipients. During (constant) mixing the solvents are evaporated by means of vacuum. The Rapamycin will be evenly distributed over the carrier material. In most cases a granulate is obtained after drying which can be milled accordingly and subsequently dry mixed with additional excipients (filler/binder/disintegrant/glidant/flavors) in order to make tablets with a suitable disintegration time and taste. An example of this formulation is shown in Table 4.

TABLE 4

| Compound | % w/w per formulation |
| --- | --- |
| Rapamycin | 1 |
| Lactose | 65 |
| Microcrystalline cellulose | 28 |
| Sodium starch glycolate | 5 |
| Artificial Beef Flavor | 0.5 |
| Magnesium stearate | 0.5 |

Example 2C: Silica Loading (Via Solvent Evaporation Process)

Create a binary system by dissolving the Rapamycin in an organic solvent and absorb on a silica carrier material under constant mixing. After full absorption, the solvents are evaporated by means of vacuum and (if required) elevated temperatures. The Rapamycin will be evenly distributed over the carrier material. In most cases a fine powder is obtained that could directly be used for a direct compression process (DC). In case a granulate is obtained it can be milled accordingly and subsequently mixed with additional excipients (filler/binder/disintegrant/glidant/flavours) in order to make tablets with a suitable disintegration time. An example of this formulation is shown in Table 5.

TABLE 5

| Compound | % w/w per formulation |
| --- | --- |
| Rapamycin | 1 |
| Silica | 9 |
| Lactose | 42 |
| Microcrystalline cellulose | 42 |
| Sodium starch glycolate | 5 |
| Artificial Beef Flavor | 0.5 |
| Magnesium stearate | 0.5 |

Example 2D: Silica Loading (Via Dry Loading Process)

Silica loading via the solvent evaporation method is a broadly known technique. The exclusion of solvents for silica loading is a relatively new approach that has many advantages over the currently existing method. Dry loading of the Rapamycin on silica can be done via high shear mixing or extrusion. A binary system can be obtained by mixing the Rapamycin with a silica carrier material. After full absorption, the dry mixture can be directly applied for a direct compression process as described under Example 2. An example of this formulation is shown in Table 6.

TABLE 6

| Compound | % per formulation |
| --- | --- |
| Rapamycin | 1 |
| Silica | 9 |
| Lactose | 42 |
| Microcrystalline cellulose | 42 |
| Sodium starch glycolate | 5 |
| Artificial Beef Flavor | 0.5 |
| Magnesium stearate | 0.5 |

Example 2E: Lyotablet (Via Freezedrying Process)

For ease of administration and possible enhanced bioavailability a Lyotablet can be a suitable formulation. In this case the Rapamycin is dissolved/dispersed in an aqueous solvent and mixed with additional excipients. The mixture is formulated in a tablet that is subsequently freeze-dried. The dried tablet is ready for use and needs no further processing. An example of this formulation is shown in Table 7.

TABLE 7

| Compound | % per formulation |
| --- | --- |
| Rapamycin | 1 |
| Gelatin | 40 |
| Mannitol | 58 |
| Artificial Beef Flavor | 0.5 |

Example 3: Stability Study

Enteric coated rapamycin formulations of similar to those of Example 1 were stored in blister packs for up to six months under various conditions. The tested formulations contain less alpha-tocopheryl acetate and the amounts of the other excipients are adjusted accordingly. These changes are not expected to affect the stability of rapamycin. Table 8 shows the stability, as measured by HPLC, of the rapamycin formulations of Example 1. Tables 9-11 show the amount of impurities found at the reported time points.

TABLE 8

| Condition | Tablet | Initial | 1 mo. | 2 mo. | 3 mo. | 6 mo. |
|---|---|---|---|---|---|---|
| 25° C. ± 2° C. | 0.3 mg | 97.0% | — | — | 98.1% | 100.5% |
| 60% ± 5% RH | 1.2 mg | 97.8% | — | — | 98.8% | 99.8% |
| | 2.4 mg | 102.7% | — | — | 99.8% | 98.7% |
| 30° C. ± 2° C. | 0.3 mg | 97.0% | — | — | 97.9% | 97.3% |
| 65% ± 5% RH | 1.2 mg | 97.8% | — | — | 97.4% | 99.7% |
| | 2.4 mg | 102.7% | — | — | 100.5% | 98.2% |
| 40° C. ± 2° C. | 0.3 mg | 97.0% | 97.6% | 96.7% | 97.0% | 98.0% |
| 75% ± 5% RH | 1.2 mg | 97.8% | 96.7% | 97.2% | 97.0% | 94.6% |
| | 2.4 mg | 102.7% | 100.1% | 99.6% | 98.2% | 98.8% |

TABLE 9

| Rapamycin Isomer C | Tablet | Initial | 1 mo. | 2 mo. | 3 mo. | 6 mo. |
|---|---|---|---|---|---|---|
| 25° C. ± 2° C. | 0.3 mg | 1.65% | — | — | 1.82% | 1.83% |
| 60% ± 5% RH | 1.2 mg | 3.56% | — | — | 3.62% | 3.38% |
| | 2.4 mg | 3.80% | — | — | 3.76% | 3.53% |
| 30° C. ± 2° C. | 0.3 mg | 1.65% | — | — | 1.91% | 1.80% |
| 65% ± 5% RH | 1.2 mg | 3.56% | — | — | 3.60% | 3.40% |
| | 2.4 mg | 3.80% | — | — | 3.78% | 3.54% |
| 40° C. ± 2° C. | 0.3 mg | 1.65% | 1.95% | 1.96% | 1.95% | 1.92% |
| 75% ± 5% RH | 1.2 mg | 3.56% | 3.61% | 3.73% | 3.64% | 3.42% |
| | 2.4 mg | 3.80% | 3.56% | 3.85% | 3.68% | 3.49% |

TABLE 10

| Rapamycin Isomer A | Tablet | Initial | 1 mo. | 2 mo. | 3 mo. | 6 mo. |
|---|---|---|---|---|---|---|
| 25° C. ± 2° C. | 0.3 mg | 0.20% | — | — | 0.15% | 0.05% |
| 60% ± 5% RH | 1.2 mg | 0.11% | — | — | 0.14% | 0.09% |
| | 2.4 mg | 0.10% | — | — | 0.14% | 0.09% |
| 30° C. ± 2° C. | 0.3 mg | 0.20% | — | — | 0.15% | 0.10% |
| 65% ± 5% RH | 1.2 mg | 0.11% | — | — | 0.14% | 0.08% |
| | 2.4 mg | 0.10% | — | — | 0.14% | 0.10% |
| 40° C. ± 2° C. | 0.3 mg | 0.20% | 0.08% | 0.09% | 0.14% | 0.09% |
| 75% ± 5% RH | 1.2 mg | 0.11% | 0.09% | 0.16% | 0.14% | 0.07% |
| | 2.4 mg | 0.10% | 0.11% | 0.11% | 0.13% | 0.09% |

TABLE 11

| Total Rapamycin Impurities (excl. A & C) | Tablet | Initial | 1 mo. | 2 mo. | 3 mo. | 6 mo. |
|---|---|---|---|---|---|---|
| 25° C. ± 2° C. | 0.3 mg | 0.15% | — | — | 0.33% | 0.27% |
| 60% ± 5% RH | 1.2 mg | 0.11% | — | — | 0.16% | 0.03% |
| | 2.4 mg | 0.07% | — | — | 0.17% | 0.15% |
| 30° C. ± 2° C. | 0.3 mg | 0.15% | — | — | 0.26% | 0.20% |
| 65% ± 5% RH | 1.2 mg | 0.11% | — | — | 0.17% | 0.05% |
| | 2.4 mg | 0.07% | — | — | 0.15% | 0.06% |
| 40° C. ± 2° C. | 0.3 mg | 0.15% | 0.21% | 0.29% | 0.45% | 0.35% |
| 75% ± 5% RH | 1.2 mg | 0.11% | 0.17% | 0.16% | 0.21% | 0.14% |
| | 2.4 mg | 0.07% | 0.12% | 0.14% | 0.24% | 0.07% |

Rapamycin stability is measure by storing the tablets comprising 2.4 mg, 1.2 mg, or 0.4 mg rapamycin according to the formulations of Example 1. The tablets are placed into individual blister packs and stored under one of the following conditions: 25° C.±2° C. 60%±5% RH; 30° C.±2° C. 65%±5% RH; and 40° C.±2° C. 75%±5% RH. Tablets are retrieved at pre-selected time points (e.g., 1 month, 2 months, 3 months, 6 months, etc.) and the amount of rapamycin and its degradation products (e.g. isomer C and isomer A) are measured by HPLC.

Example 4: Pharmacokinetics Study

Previous work has assessed the dosing, safety, and effects of 0.05 or 0.1 mg/kg rapamycin administration over ten weeks in healthy dogs (Urfer, *Geroscience,* 2017), and the pharmacokinetics of oral 0.1 mg/kg rapamycin (Larsen, *Am J Vet Res,* 2016). Based on this work, pharmacokinetic simulations were conducted by the inventors. The pharmacokinetic model was an extravascular two compartmental clearance model, represented in FIG. 1. Table 12 provides the estimates used in the simulation.

TABLE 12

| Pharmacokinetic Parameter | Mean Estimate |
|---|---|
| $K_a$ (h−1) | 0.358 |
| Cl/f (L · h/kg) | 0.651 |
| $V_1$/f (L/kg) | 6.74 |
| Q/f (L · h/kg) | 1.02 |
| $V_2$/f (L/kg) | 18.1 |

Figure 2B:
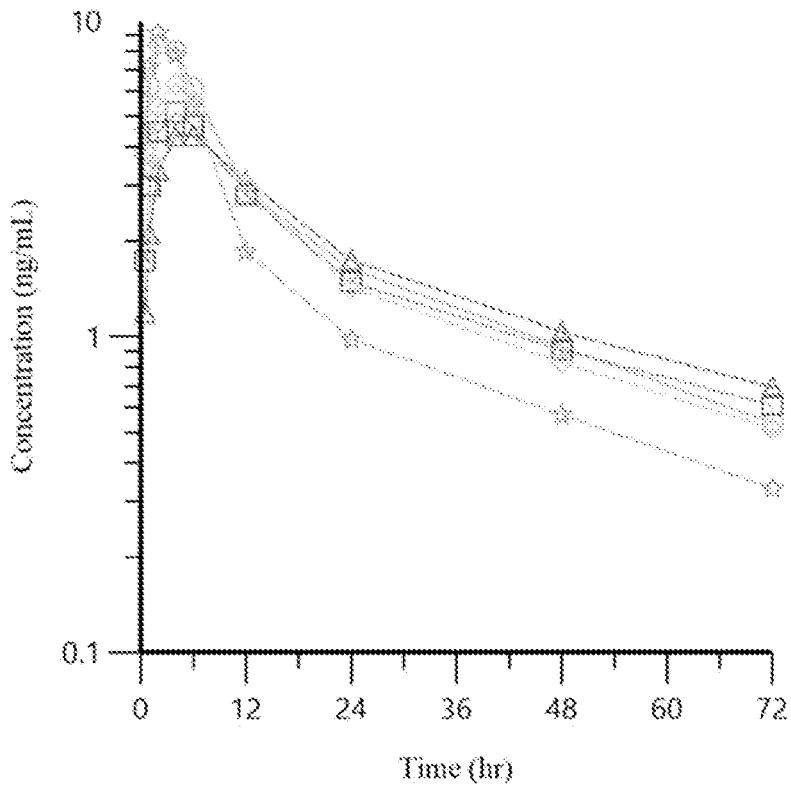
FIGS. 2B and 2C show simulated in vivo rapamycin concentration in dogs.
Figure 2C:
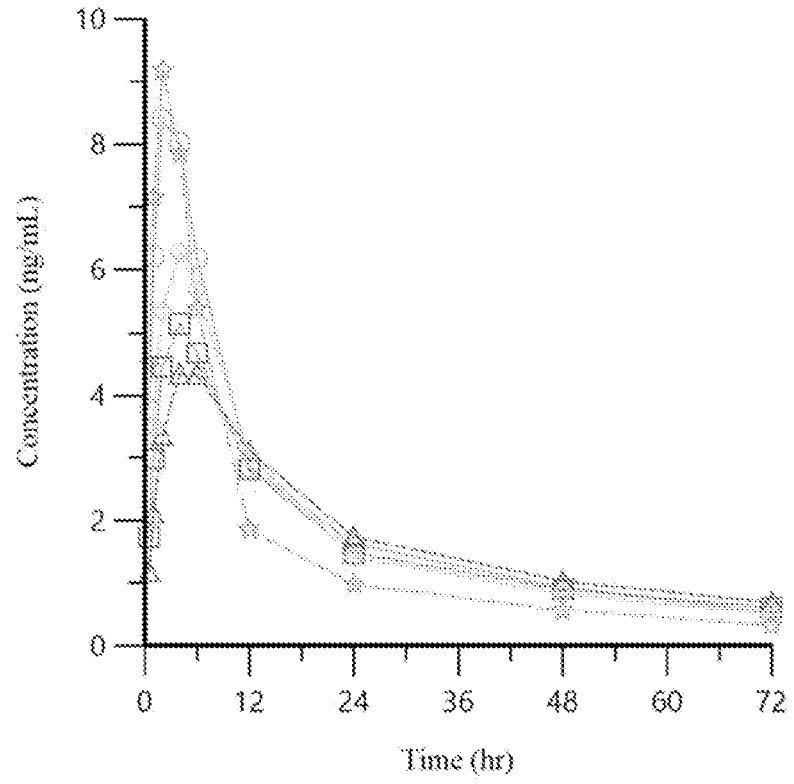
Figure 3A:
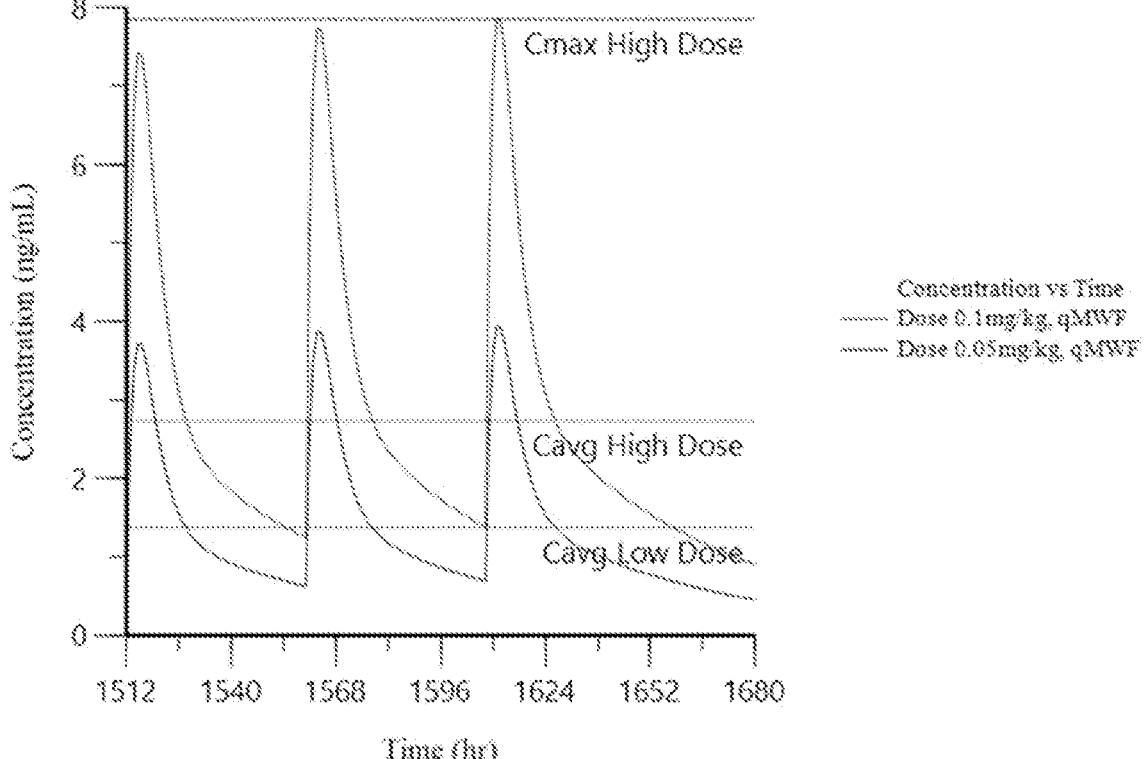
FIGS. 3A, 3B, 3C and 3D illustrate the simulated in vivo rapamycin concentration following repeated dosings.

Pharmacokinetic concentrations versus time profiles were simulated based on single or weekly dosing schedule of Monday, Wednesday, and Friday administration (3 single dose administrations over a 7 day period). The results of the simulation are shown in FIGS. 2B, 2C, and 3A.

This model has been validated with available published PK data. Using the model, we have evaluated the dose versus clinical response in a published clinical study and will use this data to predict the dose levels of Rapamycin to be used in the Triviumvet clinical efficacy and safety studies.

Figure 2A:
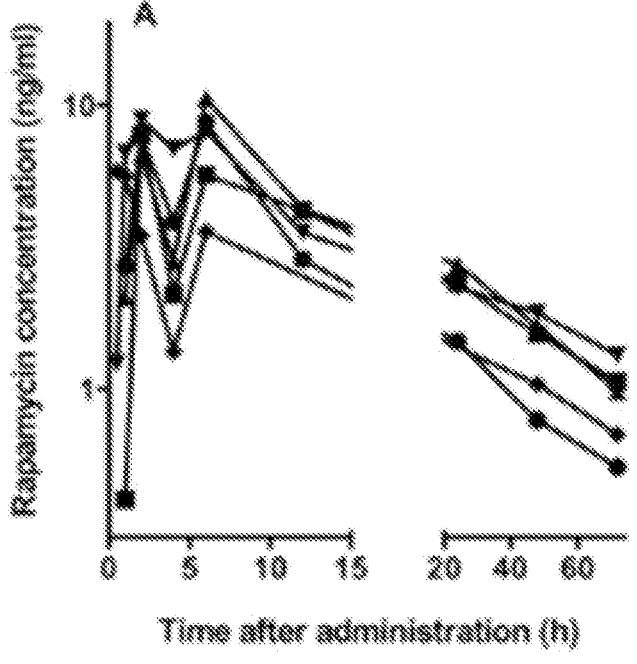
FIG. 2A shows the in vivo rapamycin concentration in dogs following administration of the drug.

The in vivo pharmacokinetic results were in accordance with a simulation study (FIG. 2A). In the simulation study, 10 weeks of rapamycin treatment at either 0.05 or 0.1 mg/kg delivered orally three times per week did not cause significant clinical side effects or abnormal hematological changes but did result in favorable changes in cardiac left ventricular function during both diastole and systole. The pharmacokinetic simulations were conducted using pharmacokinetic software (Phoenix WinNonlin™, Version 8, Certara USA) and were based on an extravascular two compartmental clearance model.

Figure 3B:
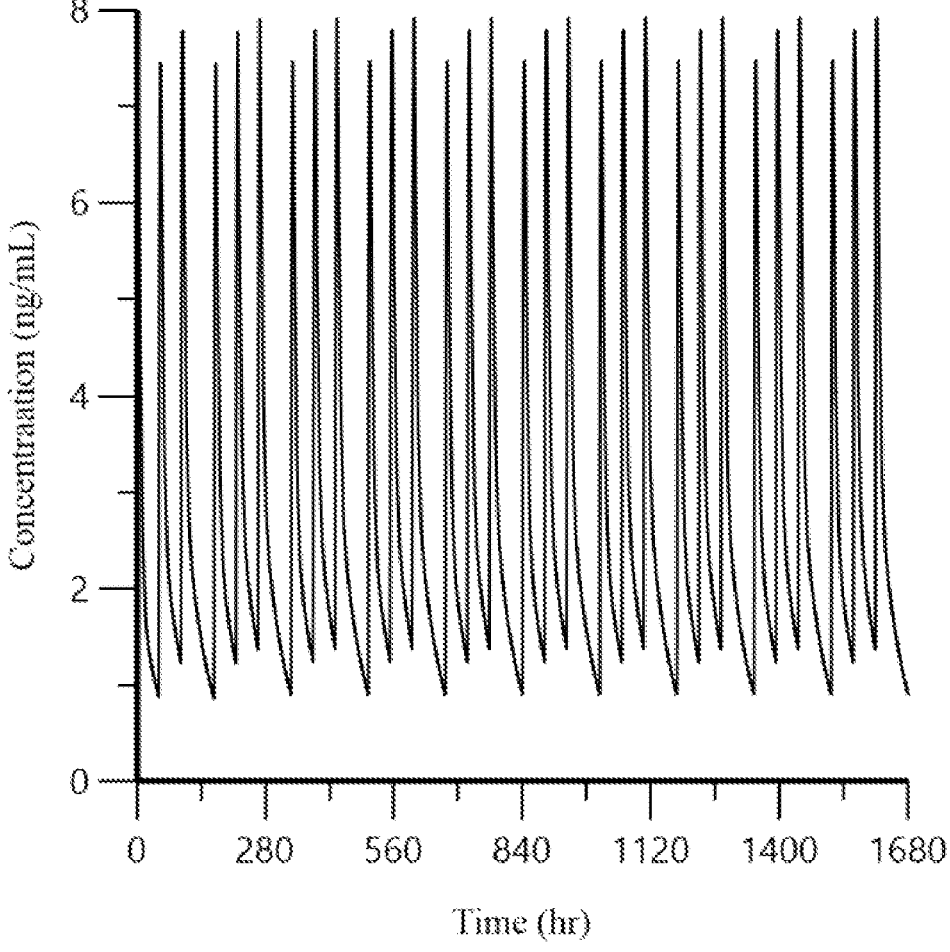
Figure 3C:
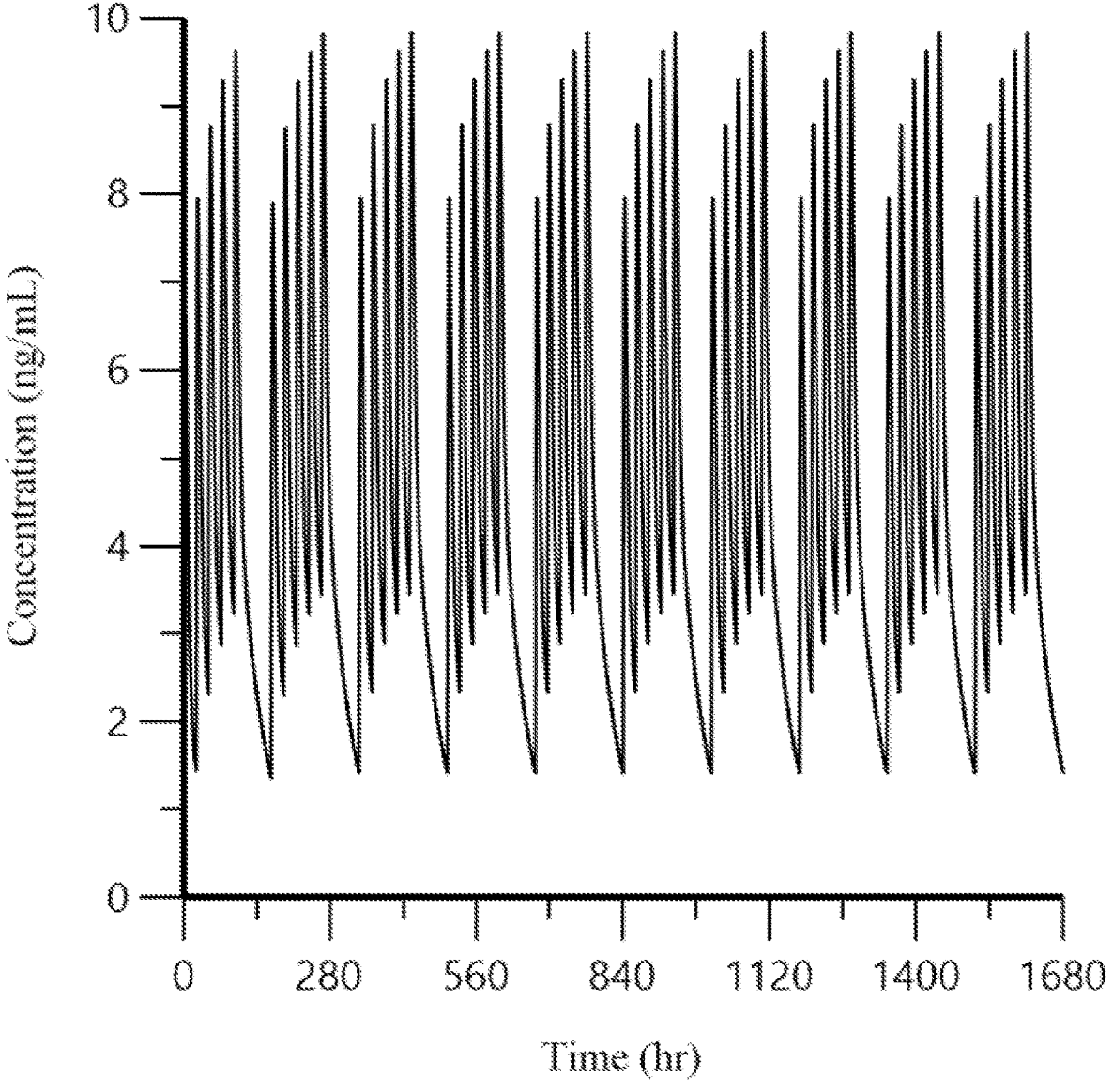
Figure 3D:
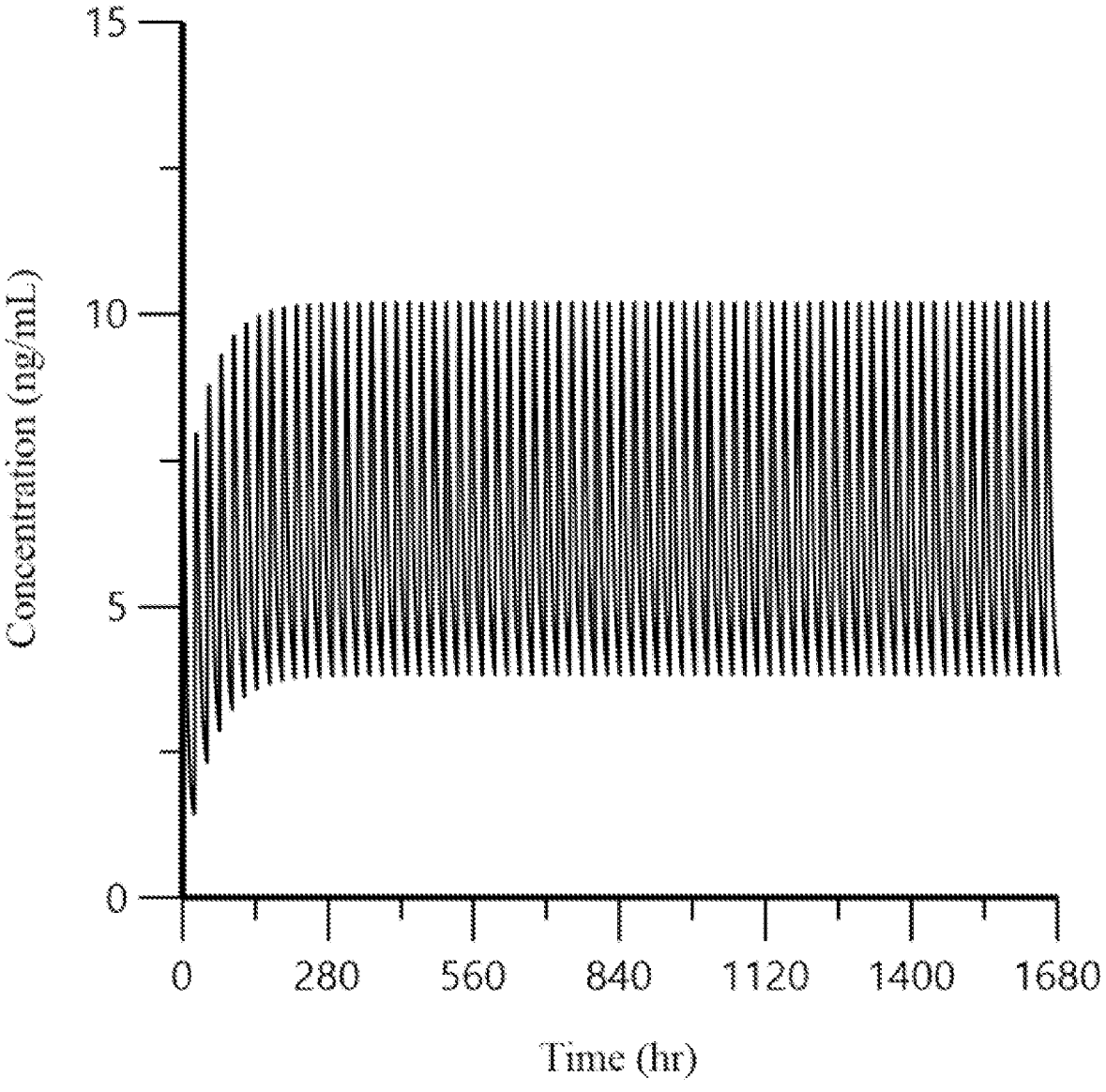
Figure 4:
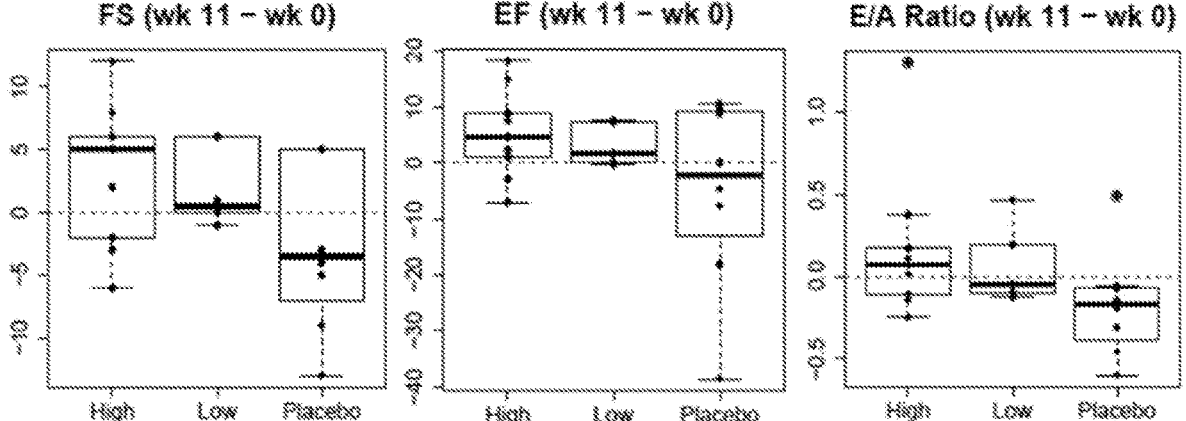
FIG. 4 shows the clinical outcomes following rapamycin administration in dogs.

The simulated rapamycin concentrations at a dose level of 0.1 mg/kg demonstrate that the administration of rapamycin using a novel dosing regimen of Monday, Wednesday, and Friday each week, resulted in simulated plasma weekly profile on Week #10 comparable to that predicted following administration on Week #1 (FIG. 3B). FIGS. 3C and 3D show a simulated plasma profiles over a ten week period for a five day per week (Monday, Tuesday, Wednesday, Thursday, and Friday) and seven days per week, respectively. This novel dosing regimen with its significant nadir in plasma concentrations is expected to mitigate side effects including hematological changes whilst at the same time enabling a significant improvement in certain cardiac functioning (including the echocardiographic parameters—fractional shortening and E/A ratio). See FIG. 4.

Example 5: In Vivo Canine Studies

Figure 5:
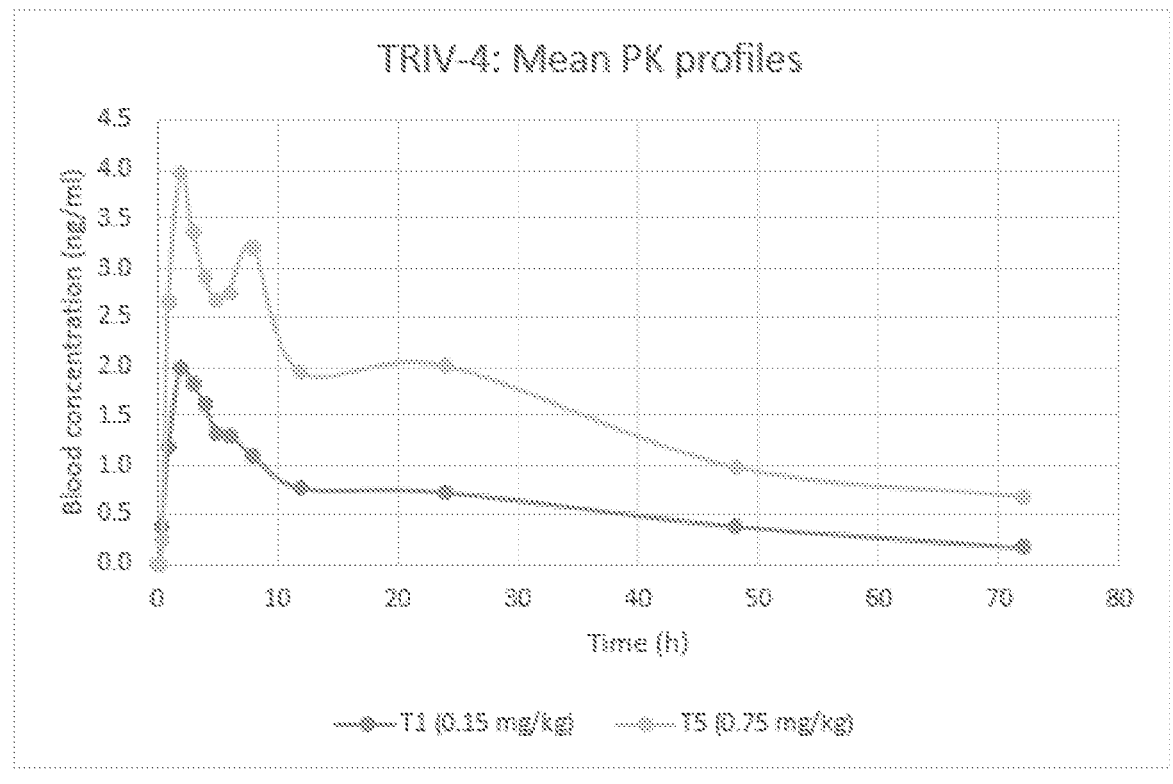
FIG. 5 shows the rapamycin blood concentration in dogs following oral administration of the drug at 0.15 mg/kg or 0.75 mg/kg.

Dogs were orally administered enteric coated formulations at 0.15 mg/kg (T1) and 0.75 mg/kg (T5) rapamycin dosage levels. The pharmacokinetic profile of this study is provided in Table 13. FIG. 5 shows the mean rapamycin blood concentration (ng/mL) of the T1 and T5 formulations.

TABLE 13

| Parameter | Dose Group | N[†] | Arith. Mean | SD | Median | Min | Max |
|---|---|---|---|---|---|---|---|
| $AUC_{0-\infty}$, | T1 | 4 | 42.67 | 33.87 | 38.52 | 10.59 | 83.05 |
| hr*ng/mL | T5 | 5 | 102.23 | 61.11 | 98.41 | 37.69 | 190.65 |
| $AUC_{tlast}$, | T1 | 6 | 40.77 | 27.19 | 45.16 | 5.29 | 73.63 |
| hr*ng/mL | T5 | 6 | 110.60 | 79.41 | 96.88 | 26.50 | 239.46 |
| $C_{max}$, ng/mL | T1 | 6 | 2.23 | 0.99 | 2.17 | 1.10 | 3.66 |
|  | T5 | 6 | 4.41 | 2.94 | 3.14 | 2.00 | 9.24 |
| $k_{elim}$, 1/h | T1 | 4 | 0.0596 | 0.0355 | 0.0627 | 0.0227 | 0.0903 |
|  | T5 | 5 | 0.0357 | 0.0087 | 0.0338 | 0.0273 | 0.0501 |
| $t_{1/2}$, h | T1 | 4 | 16.35 | 10.97 | 13.59 | 7.67 | 30.56 |
|  | T5 | 5 | 20.25 | 4.29 | 20.52 | 13.84 | 25.38 |
| $t_{max}$, h | T1 | 6 | 1.83 | 0.75 | 2.00 | 1.00 | 3.00 |
|  | T5 | 6 | 2.17 | 0.75 | 2.00 | 1.00 | 3.00 |

Figure 6:
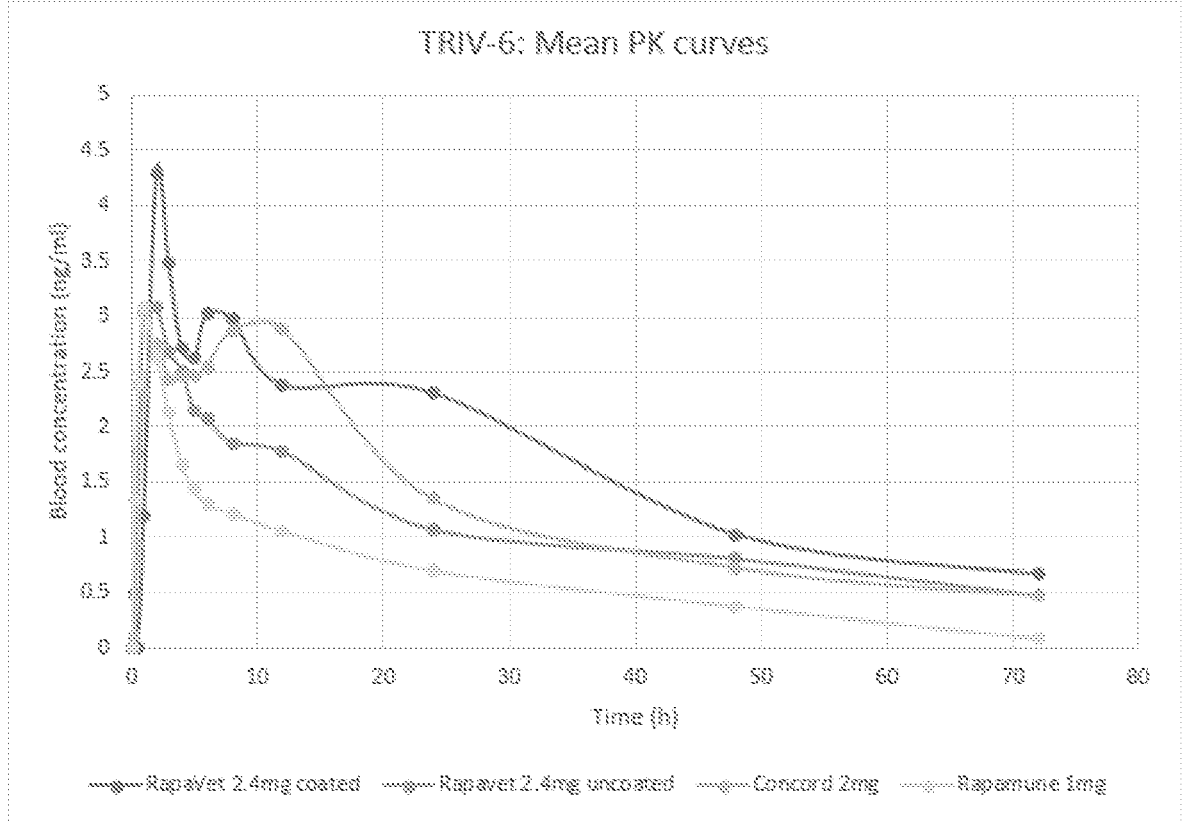
FIG. 6 shows the rapamycin blood concentration in dogs following oral administration of enterically coated, uncoated, non-enterically coated, and reference rapamycin formulations.

The pharmacokinetic profiles of rapamycin formulations comprising an enteric coating (2.4 mg rapamycin), lacking an enteric coating (2.4 mg rapamycin), comprising a non-functional enteric coating (2.0 mg rapamycin), and a reference formulation (1 mg Rapamune) were measured following oral administration in dogs. The pharmacokinetic profile of the formulations is shown in Table 14. FIG. 6 shows the mean rapamycin blood concentration (ng/mL).

TABLE 14

| PK Parameters | Enteric coating | | No enteric coating 2 | | Non-functional coating | | Reference | |
|---|---|---|---|---|---|---|---|---|
|  | Mean | SD | Mean | SD | Mean | SD | Mean | SD |
| $T_{max}$ (h) | 2.5 | NA | 1 | NA | 1.5 | NA | 1.5 | NA |
| $C_{max}$ (ng/mL) | 6.04 | 5.12 | 4.03 | 1.27 | 3.76 | 2.21 | 3.26 | 1.91 |
| $AUC_{0-72\ h}$ (ng · h/mL) | 51.65 | 25.23 | 32.13 | 6.39 | 42.74 | 28.62 | 47.32 | 12.15 |
| $T_{1/2}$ (h) | 19.8 | NC | 32.69 | NC | 17.77 | NC | 40.76 | NC |

Figure 7:
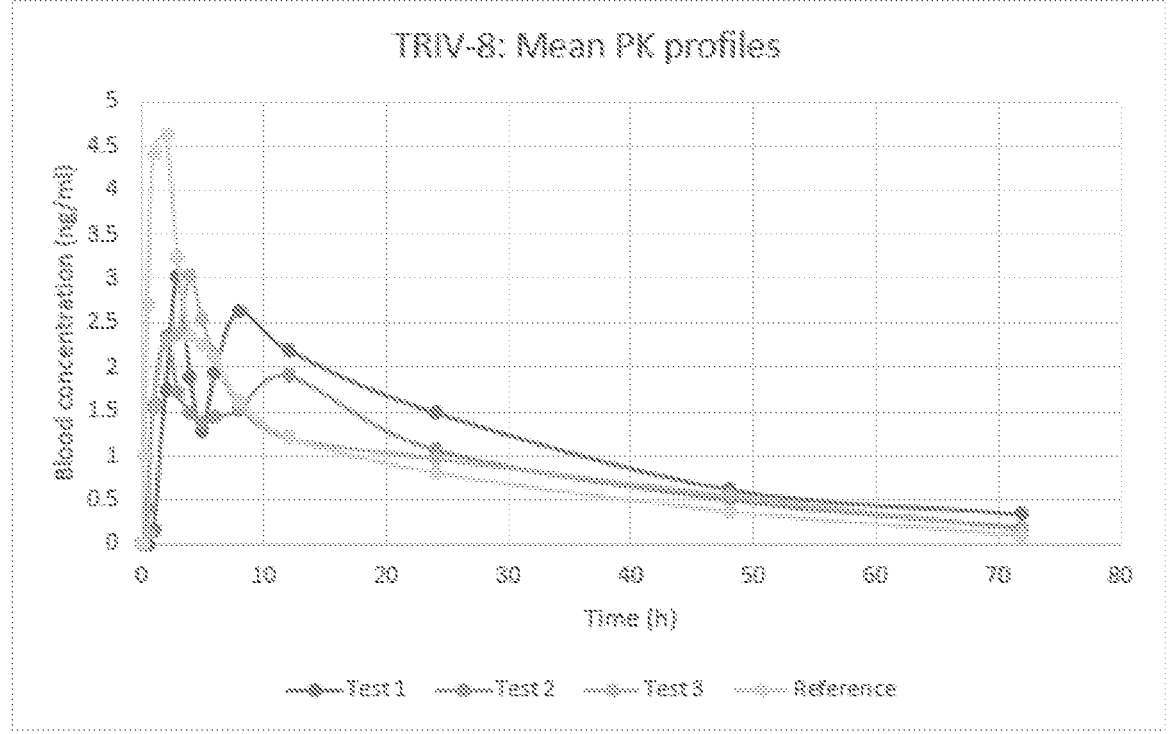
FIG. 7 shows the rapamycin blood concentration in dogs following oral administration of different formulations of rapamycin.

The pharmacokinetic profile of different formulations of rapamycin was determined by orally administering to dogs rapamycin formulations comprising an enteric coating with a particular API particle size, nonfunctional coating of same API particle size, enteric coating with an altered particle size, and a reference formulation (Rapamune 2 mg). The pharmacokinetic profile of these formulations is presented in Table 15. FIG. 7 shows the mean rapamycin blood concentration (ng/mL).

TABLE 15

| PK Parameters | Enteric coating - particle size A (2.4 mg) | | Nonfunctional coating - particle size A (2.4 mg) | | Enteric coating - particle size B (2.4 mg) | | Reference (2.0 mg) | |
|---|---|---|---|---|---|---|---|---|
|  | Mean | SD | Mean | SD | Mean | SD | Mean | SD |
| $T_{max}$ (h) | 3 | NA | 3 | NA | 4 | NA | 2 | NA |
| $C_{max}$ (ng/mL) | 4.15 | 4.29 | 3.55 | 2.37 | 4.41 | 2.51 | 5.50 | 2.48 |
| $AUC_{0-72\ h}$ (ng · h/mL) | 97.37 | 104.98 | 56.84 | 67.02 | 54.41 | 37.85 | 52.45 | 32.31 |
| $AUC_{0-inf}$ (ng · h/mL) | 112.47 | 126.20 | 80.36 | 91.71 | 92.06 | 55.33 | 75.15 | 40.17 |
| $T_{1/2}$ (h) | 12.60 | 6.77 | 19.72 | 15.03 | 32.35 | 20.03 | 22.21 | 15.18 |
| $K_{el}$ (1/h) | 0.072 | 0.042 | 0.071 | 0.069 | 0.028 | 0.013 | 0.046 | 0.03 |

Example 6: In Vivo Feline Studies

Figure 8:
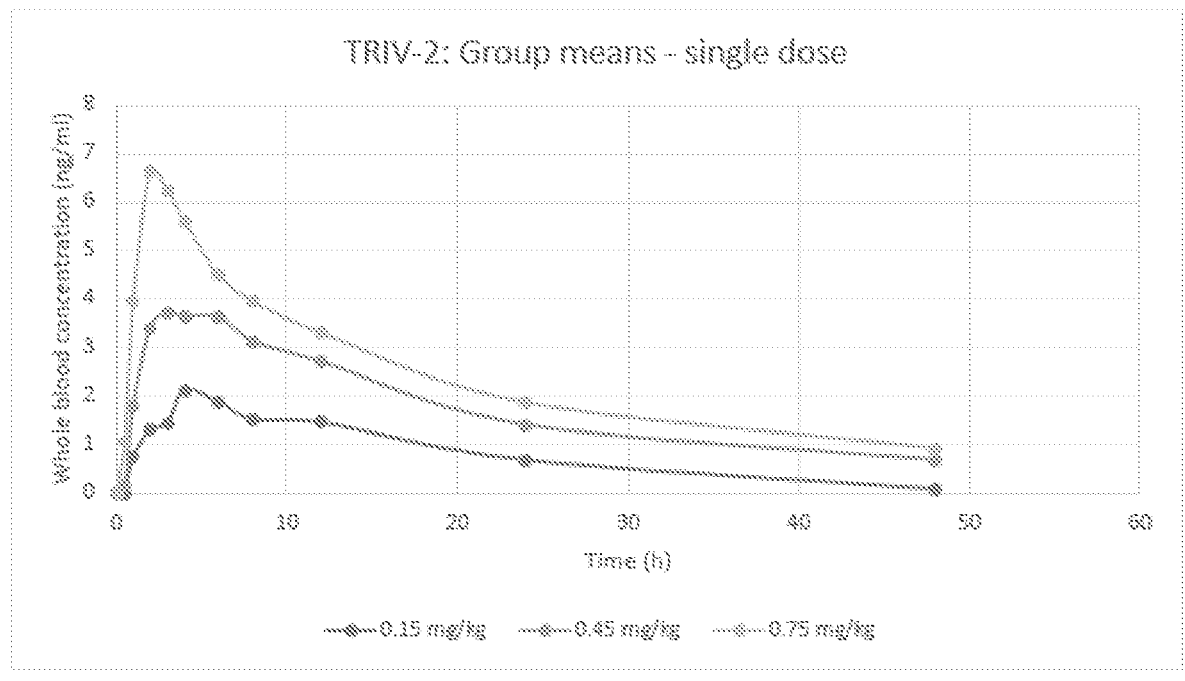
FIG. 8 shows the rapamycin blood concentration following a single oral administration of 0.15 mg/kg, 0.45 mg/kg, and 0.75 mg/kg in cats.
Figure 9:
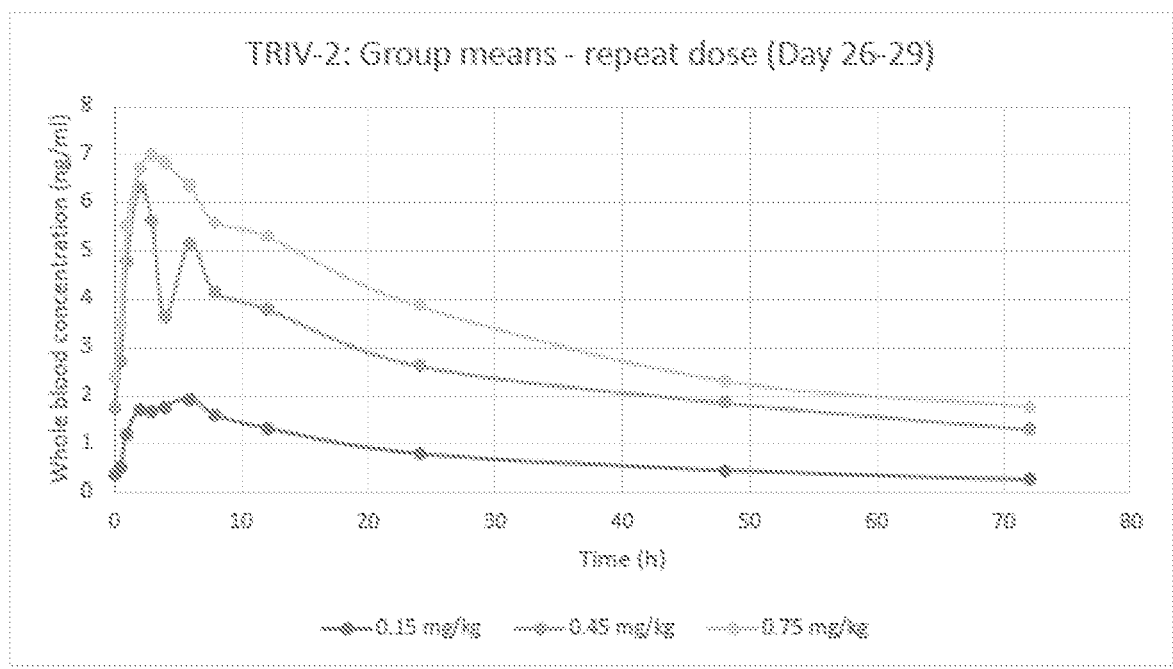
FIG. 9 shows the rapamycin blood concentration following a repeated oral dosings of 0.15 mg/kg, 0.45 mg/kg, and 0.75 mg/kg in cats.

Laboratory cats were given oral enteric-coated formulations of 0.15 mg/kg, 0.45 mg/kg, or 0.75 mg/kg rapamycin three times a week for four weeks. This represents a first-in-species repeat dose test toxicokinetic study in cats. Pharmacokinetic sampling was performed after the first and last doses. FIGS. 8 and 9 show the whole blood concentration of rapamycin for 48 hours following a single dose (FIG. 8) or for 72 hours following repeated doses (FIG. 9). Tables 16 and 17 show the Tmax, Cmax, and $AUC_{0-72}$ at Day 0 and Day 26 following rapamycin administration.

TABLE 16

| Day 0 | 0.15 mg/kg | | 0.45 mg/kg | | 0.75 mg/kg | |
|---|---|---|---|---|---|---|
|  | Mean | SD | Mean | SD | Mean | SD |
| Tmax (h) | 4 | N/A | 2.5 | N/A | 2 | N/A |
| Cmax (ng/mL) | 2.85 | 1.41 | 4.40 | 2.97 | 7.56 | 9.50 |
| $AUC_{0-72}$ (ng · h/mL) | 40.99 | 16.75 | 99.47 | 63.89 | 135.36 | 99.55 |

TABLE 17

| Day 26 | 0.15 mg/kg | | 0.45 mg/kg | | 0.75 mg/kg | |
|---|---|---|---|---|---|---|
|  | Mean | SD | Mean | SD | Mean | SD |
| Tmax (h) | 2.5 | N/A | 2 | N/A | 2 | N/A |
| Cmax (ng/mL) | 2.26 | 1.20 | 6.98 | 6.40 | 8.07 | 4.30 |
| $AUC_{0-72}$ (ng · h/mL) | 54.04 | 23.50 | 182.42 | 217.11 | 248.38 | 131.32 |

Figure 10:
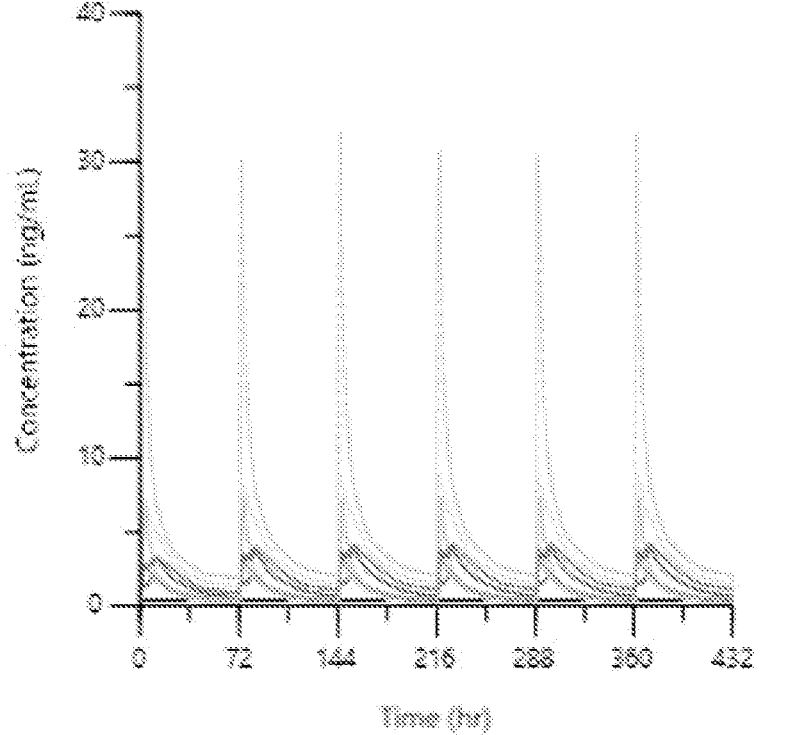
FIG. 10 shows simulated in vivo rapamycin concentration in cats following administration of the drug at a 72-hour dosing interval.
Figure 11:
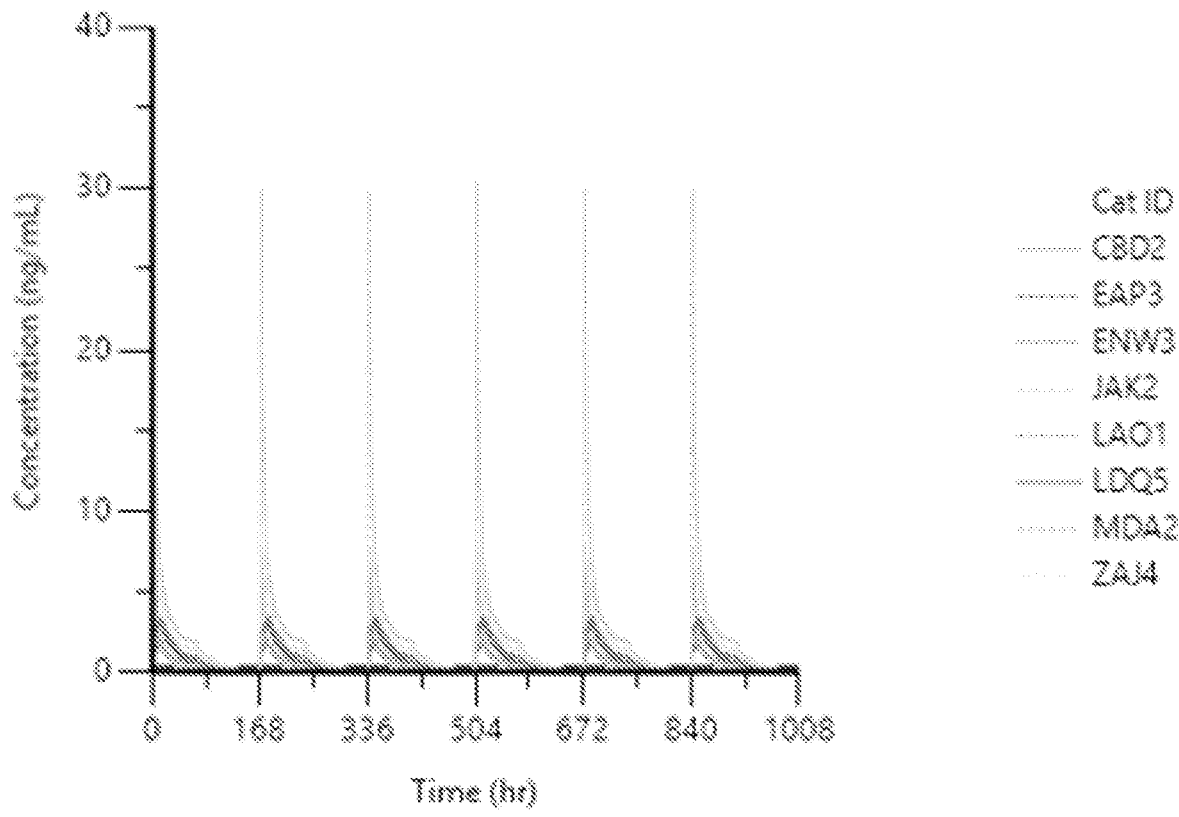
FIG. 11 shows simulated in vivo rapamycin concentration in cats following administration of the drug at a 168-hour dosing interval.

Based on the above data, the behavior of an embodiment of the invention was modeled. FIGS. 10 and 11 show the predicted concentrations in individual cats following rapamycin dosing at 72 or 168 hours, respectively.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for treating hypertrophic cardiomyopathy, dilated cardiomyopathy, mitral valve disease, or pressure-overload cardiac hypertrophy in companion animals, the method comprising: administering to the companion animal in need thereof a composition comprising; an intra-granular part comprising rapamycin, rapalog, or a salt thereof in a dispersion comprising a binder, and a polymer, an extra-granular part comprising a polymer, and a delayed release coating, wherein the composition is administered to the companion animal once per week at a dosing amount of the rapamycin, rapalog, or salt thereof from about 0.025 mg/kg to about 0.75 mg/kg.

2. The method of claim 1, wherein rapamycin, or salt thereof, is administered.

3. The method of claim 1, wherein the rapalog is selected from the group consisting of temsirolimus, everolimus, and ridaforolimus.

4. The method of claim 1, wherein the composition comprises a coating comprising methacrylic acid ethyl acrylate copolymer, talc, titanium dioxide, triethyl citrate, colloidal anhydrous silica, sodium bicarbonate, sodium lauryl sulfate and, one or more colorants.

5. The method of claim 1, wherein the polymer of the rapamycin dispersion and the polymer of the extra-granular part are independently selected from the group consisting of microcrystalline cellulose, hydroxypropyl methylcellulose, polyvinyl pyrrolidone, crospovidone, povidone, polyplasdone, and combinations thereof.

6. The method of claim 1, wherein the binder is selected from the group consisting of poloxamer, glyceryl mono-oleate, alpha-DL-tocopheryl acetate, povidone, citric acid anhydrous, and combinations thereof.

7. The method of claim 1, wherein the dispersion further comprises a sugar.

8. The method of claim 1, wherein the dispersion comprises microcrystalline cellulose, poloxamer, and tocopheryl acetate.

9. The method of claim 8, wherein the dispersion further comprises sucrose, glyceryl mono-oleate, povidone K-30, and citric acid anhydrous.

10. The method of claim 1, wherein the dispersion has a D90 of about 2 to about 30 pm.

11. The method of claim 10, wherein the dispersion has a D90 of about 2 pm to about 5 pm.

12. The method of claim 1, wherein the extra-granular part comprises microcrystalline cellulose, crospovidone, and talc.

13. The method of claim 1, wherein the composition comprises about 1% to about 10% binder, about 40% to about 75% polymer, and about 20% to about 40% sugar, based on the total weight of the composition.

14. The method of claim 1, wherein the intra-granular part comprises rapamycin, rapalog, or a salt thereof, microcrystalline cellulose, crospovidone, and sucrose, wherein the binder comprises poloxamer, glyceryl mono-oleate, alpha-DL-tocopheryl acetate, povidone K-30, or citric acid anhydrous; wherein the extra-granular part comprises microcrystalline cellulose, crospovidone, and talc; and wherein the composition further comprises a coating comprising methacrylic acid ethyl acrylate copolymer, talc, titanium dioxide, triethyl citrate, colloidal anhydrous silica, sodium bicarbonate, sodium lauryl sulfate and, one or more colorants.

15. The method of claim 1, wherein the companion animal is a dog or a cat.

* * * * *